United States Patent
Lee

(10) Patent No.: US 9,386,958 B2
(45) Date of Patent: Jul. 12, 2016

(54) INTRA-ORAL X-RAY IMAGING DEVICE EQUIPPED WITH CAMERA

(75) Inventor: Rena Lee, Seoul (KR)

(73) Assignee: EWHA UNIVERSITY-INDUSTRY COLLABORATION FOUNDATION (KR)

( * ) Notice: Subject to any disclaimer, the term of this patent is extended or adjusted under 35 U.S.C. 154(b) by 317 days.

(21) Appl. No.: 14/000,979

(22) PCT Filed: Feb. 9, 2012

(86) PCT No.: PCT/KR2012/000958
§ 371 (c)(1),
(2), (4) Date: Oct. 10, 2013

(87) PCT Pub. No.: WO2012/115372
PCT Pub. Date: Aug. 30, 2012

(65) Prior Publication Data
US 2014/0050298 A1    Feb. 20, 2014

(30) Foreign Application Priority Data
Feb. 25, 2011 (KR) .................. 10-2011-0016841

(51) Int. Cl.
*A61B 6/14* (2006.01)
*A61B 6/00* (2006.01)

(52) U.S. Cl.
CPC .............. *A61B 6/145* (2013.01); *A61B 6/4405* (2013.01); *A61B 6/4429* (2013.01)

(58) Field of Classification Search
CPC ...... A61B 5/0088; A61B 5/6844; A61B 6/14; A61B 6/145; A61B 6/4429; A61B 6/4405
See application file for complete search history.

(56) References Cited

U.S. PATENT DOCUMENTS

| | | | | |
|---|---|---|---|---|
| 4,259,583 A | * | 3/1981 | Albert | A61B 6/145 378/147 |
| 4,783,793 A | * | 11/1988 | Virta | A61B 6/14 378/38 |
| 5,008,547 A | * | 4/1991 | Molteni | G01T 1/2018 250/368 |
| 7,278,787 B2 | | 10/2007 | Hack et al. | |

(Continued)

FOREIGN PATENT DOCUMENTS

| | | | | |
|---|---|---|---|---|
| GB | 1532502 A | * | 11/1978 | A61B 6/08 |
| JP | 2004344260 | | 12/2004 | |

(Continued)

OTHER PUBLICATIONS

International Search Report—PCT/KR2012/000958 dated Sep. 24, 2012.

*Primary Examiner* — Glen Kao
(74) *Attorney, Agent, or Firm* — Cantor Colburn LLP

(57) ABSTRACT

Provided is an intraoral X-ray imaging apparatus having a camera, including: a frame; an X-ray irradiator which is installed to be supported by the frame and of which the one end portion is inserted into the oral cavity and which irradiates X-ray through an X-ray irradiation hole formed on the one end portion inserted into the oral cavity; a camera unit which is installed at the one end portion of the X-ray irradiator to image an interior of the oral cavity; a monitor unit which is connected to a camera unit to output the image captured by the camera unit; and an X-ray detector which is arranged to be separated from the X-ray irradiator in the frame so as to detect the X-ray irradiated from the X-ray irradiator outside the oral cavity.

18 Claims, 15 Drawing Sheets

(56) References Cited

U.S. PATENT DOCUMENTS

| | | | |
|---|---|---|---|
| 2002/0067407 A1 | 6/2002 | Cooper | |
| 2005/0058258 A1* | 3/2005 | Martti | A61B 6/145 378/197 |
| 2008/0090199 A1* | 4/2008 | Noguchi | A61B 5/0088 433/29 |
| 2009/0310741 A1* | 12/2009 | Borghese | A61B 5/0064 378/37 |
| 2010/0119036 A1* | 5/2010 | Muller | A61B 6/06 378/38 |
| 2010/0177865 A1* | 7/2010 | Yoshimura | A61B 6/14 378/19 |
| 2011/0150185 A1* | 6/2011 | Uzbelger Feldman | A61B 6/14 378/191 |

FOREIGN PATENT DOCUMENTS

| | | |
|---|---|---|
| JP | 2005519719 | 7/2005 |
| JP | 4732332 | 7/2011 |
| KR | 1020090053568 | 5/2009 |

* cited by examiner

INTRA-ORAL X-RAY IMAGING DEVICE EQUIPPED WITH CAMERA

TECHNICAL FIELD

The present invention relates to an intraoral X-ray imaging apparatus having a camera, and more particularly, to an intraoral X-ray imaging apparatus having a camera capable of obtaining an accurate image having constant magnification in the case of obtaining a panoramic image for dental treatment by using an X-ray irradiator with a low X-ray dose located inside an oral cavity.

BACKGROUND ART

In general, an X-ray imaging apparatus for identifying a state of an alveolar bone (teeth-associated structure) including teeth for teeth/periodontal disease treatment and orthodontic treatment is installed in a dental clinic.

An operator (or a dentist) uses the X-ray imaging apparatus to identify the size and shape of the jawbone and an anatomical change of the jawbone in the horizontal and vertical axes through radiological tests and to consider disease factors existing in the jawbone and information influencing medical treatment. The image information is important in all the processes for optimal dental treatment and long-term success after the dental treatment.

The X-ray (radiation) irradiations method as the X-ray imaging method include, for example, a panoramic imaging (panoramic X-ray imaging) method of two-dimensionally imaging an alveolar bone including teeth, a CT imaging (computerized tomography imaging) method of three-dimensionally imaging the alveolar bone including teeth with a higher accuracy, and a cephalometric imaging method of imaging the head of a patient from the front, rear, left, and right sides.

In the related art, the X-ray imaging apparatus is configured so that an X-ray irradiator is arranged at the one side of the head of a patient and an X-ray detector is arranged at the opposite side thereof. Since X-ray emitted from the X-ray irradiator needs to pass through the entire head, the X-ray needs to have a strong intensity. In addition, since an irradiation angle of the X-ray irradiator with respect to a tooth is fixed, the image can be obtained at only the fixed angle.

Accordingly, the X-ray imaging apparatus in the related art has problems as follows. The first problem is that unnecessary radiation exposure dose may be applied to the head. The second problem is that a ghost image, that is, an image of a tooth other than the tooth of interest may exist. The third problem is that images of a tooth captured at various angles cannot be obtained. The fourth problem is that the X-ray imaging apparatus occupies a too large space.

In addition, an X-ray detector needs to be located inside the oral cavity in order to accurately image a tooth. However, in the X-ray imaging apparatus in the related art, since the size of the X-ray detector is large, a patient may feel unpleasant during the X-ray imaging.

In addition, since the imaging object tooth cannot be identified inside the oral cavity, the area of the X-ray irradiation is widened, and a radiation exposure dose applied to the head of a patient is large.

In addition, since the X-ray detector does not approach close to the tooth, the accuracy of the image may be low.

DISCLOSURE

Technical Problem

The objects of an intraoral X-ray imaging apparatus having a camera according to the present invention are as follows.

First, the present invention is to accurately image an imaging object tooth and to obtain an image having a high quality with a low X-ray dose by allowing an X-ray irradiator to be located inside the oral cavity.

Second, the present invention is to avoid confusion in image diagnosis by removing a ghost image by allowing an X-ray irradiator inside the oral cavity.

Third, the present invention is to maintain constant magnification of images of portions of a tooth by maintaining a distance between an X-ray imaging unit and an X-ray detector constant in the case where the X-ray irradiator is located inside the oral cavity during the X-ray imaging.

Fourth, the present invention is to obtain an accurate image of a tooth without distortion by allowing the X-ray detector to approach closest to the tooth in the case where the X-ray irradiator is located inside the oral cavity during the X-ray imaging.

Fifth, the present invention is to minimize a radiation exposure dose applied to the head by allowing the X-ray irradiator to irradiate a low X-ray dose.

Sixth, the present invention is to obtain images at various angles by freely adjusting an irradiation angle of the X-ray irradiator.

Seventh, the present invention is to reduce a space occupied by the X-ray imaging apparatus by reducing the size of the X-ray irradiator.

The objects of the present invention are not limited thereto. Other objects which are not mentioned above may be clearly understood from the below description by the ordinarily skilled in the related art.

Technical Solution

According to an aspect of the present invention, there is provided an intraoral X-ray imaging apparatus having a camera, including: a frame; an X-ray irradiator which is installed to be supported by the frame and of which the one end portion is inserted into the oral cavity and which irradiates X-ray through an X-ray irradiation hole formed on the one end portion inserted into the oral cavity; a camera unit which is installed at the one end portion of the X-ray irradiator to image an interior of the oral cavity; a monitor unit which is connected to a camera unit to output the image captured by the camera unit; and an X-ray detector which is arranged to be separated from the X-ray irradiator in the frame so as to detect the X-ray irradiated from the X-ray irradiator outside the oral cavity.

In addition, a light source may be installed in the X-ray irradiator to illuminate the interior of the oral cavity.

In addition, the X-ray irradiator may be configured to include: a main body which is disposed to be inserted into the oral cavity in the longitudinal direction thereof; an X-ray irradiation body which is protruded from the end portion of the main body upward or downward and is rotatably coupled to the main body and in which an X-ray irradiation hole 410 is formed; and an irradiation body rotation motor which is installed inside the main body to rotate the irradiation body, wherein the camera unit is installed in the X-ray irradiation body, and wherein the camera unit and the X-ray irradiation hole is arranged with an angle difference around a rotation center of the X-ray irradiation body.

In addition, the X-ray irradiation body may be tiltably connected to the main body.

In addition, an aperture diaphragm for adjusting an aperture size of the X-ray irradiation hole may be installed in the X-ray irradiation hole.

In addition, a plurality of the X-ray irradiation holes having different sizes may be arranged to be separated from each other with angle differences from the camera unit around the rotation center of the X-ray irradiation body so as to irradiate different X-ray doses.

In addition, a plurality of the X-ray irradiation holes may be individually opened and closed, so that only the X-ray irradiation hole directing the imaging object tooth is opened and the other X-ray irradiation holes are closed.

In addition, the camera unit and the X-ray irradiation hole may be arranged at positions with an angle difference of 180 degrees on the same circumference in the X-ray irradiation body.

In addition, the intraoral X-ray imaging apparatus may further include a supporting arm which connects the X-ray irradiator and the X-ray detector, wherein the X-ray detector is coupled to the supporting arm so as to be moved in the longitudinal direction of the supporting arm.

In addition, the intraoral X-ray imaging apparatus may further include a supporting arm which connects the X-ray irradiator and the X-ray detector, wherein a length of the supporting arm can be adjusted.

In addition, the X-ray detector may be configured to include a link member of which the one side is rotatably connected to the supporting arm and a detection panel member which is installed to the other side of the link member to detect the X-ray.

In addition, the link member is configured to include a first link which is connected to the supporting arm and a second link of which the one side is rotatably connected to the first link through a hinge connector and the other side is connected the detection panel member.

In addition, the hinge connector elastically supports the second link.

In addition, the intraoral X-ray imaging apparatus may further include a base plate which is movably installed in an upper portion of the frame and on which the base supporting member coupled to the X-ray irradiator is installed, wherein the base plate is configured to include a guide block having a groove formed in a lower portion thereof, so that the base plate is moved in the state where the guide rail coupled to the frame is inserted into the groove of the guide block.

In addition, the X-ray irradiator may be moved by a second driving unit which transmits power to the base plate by using driving means.

In addition, the intraoral X-ray imaging apparatus may further include an elevating unit which is coupled to a lower portion of the frame; and a lower frame which is coupled to a lower portion of the elevating unit.

Advantageous Effects

As described above, in an intraoral X-ray imaging apparatus having a camera according to the present invention, since an X-ray irradiator is located inside the oral cavity, it is possible to obtain an image having a high quality with a low X-ray dose and to avoid confusion in image diagnosis by removing a ghost image.

In addition, since the imaging object tooth can be accurately identified inside the oral cavity, the X-ray can be irradiated on only the imaging object tooth, so that it is possible to minimize a radiation exposure dose applied to the head of a patient.

In addition, since a distance between the X-ray irradiator and the X-ray detector is minimized, it is possible to obtain images of portions of a tooth with constant magnification and to obtain accurate images without distortion.

In addition, since an irradiation angle of the X-ray irradiator can be freely adjusted, it is possible to obtain images at various angles.

The present invention is not limited to the above-described effects. Other effects which are not mentioned above may be clearly understood from the below description by the ordinarily skilled in the related art.

BEST MODE

Hereinafter, an intraoral X-ray imaging apparatus having a camera according to a preferred embodiment of the present invention will be described in detail with reference to the attached drawings.

Figure 1:
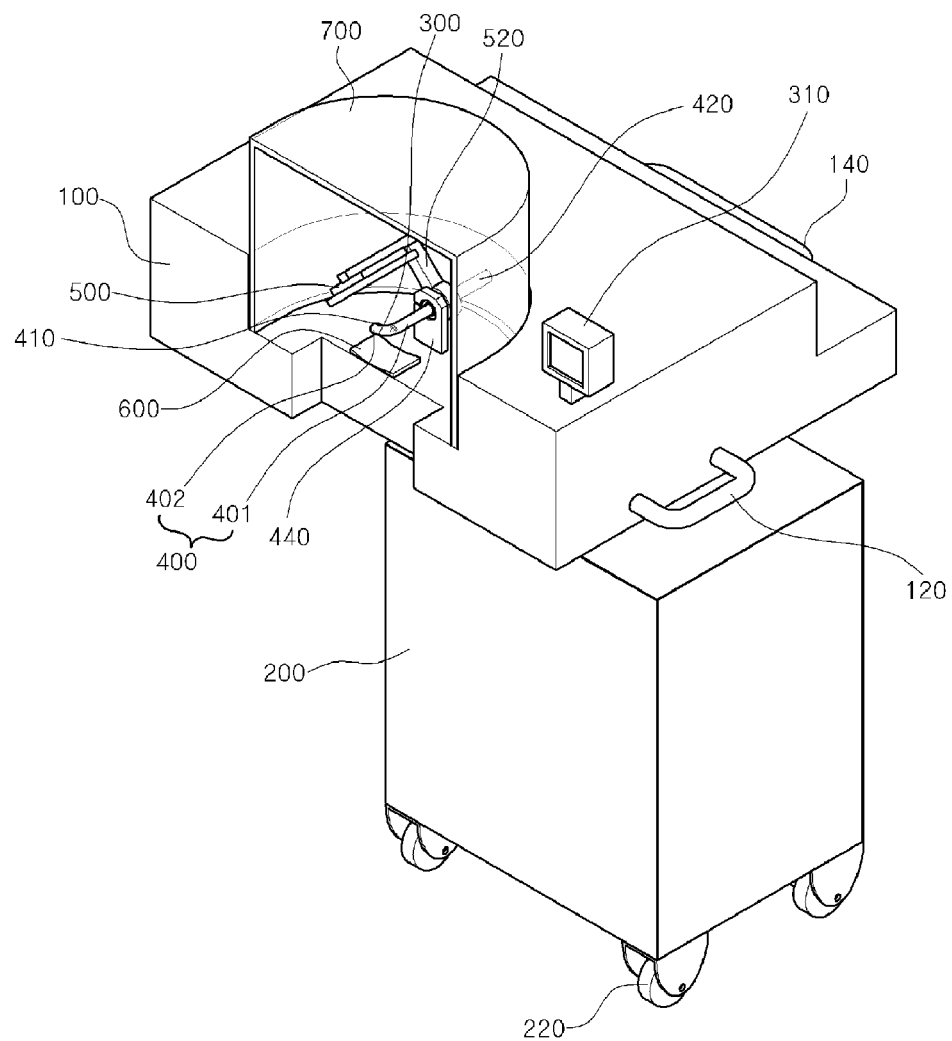
FIG. 1 is a perspective diagram illustrating an intraoral X-ray imaging apparatus having a camera according to an embodiment of the present invention.

FIG. 1 illustrates an intraoral X-ray imaging apparatus having a camera according to an embodiment of the present invention.

The intraoral X-ray imaging apparatus having a camera according to the present invention is configured to include a frame 100.

The frame 100 is provided with a grip 120, so that a patent can fix the pose by holding the grip 120.

The frame 100 is provided with a shield glass 700, so that leakage of X-ray irradiated from the X-ray irradiator 400 can be prevented. Therefore, it is possible to prevent persons other than the patient from being exposed to radiation.

The intraoral X-ray imaging apparatus having a camera according to the present invention is configured to an X-ray irradiator 400 which is installed so as to be supported by the frame 100 and of which one end portion is inserted into the oral cavity. The X-ray irradiator 400 is configured so that an X-ray irradiation hole 410 emitting X-ray is formed on the one end portion which is inserted into the oral cavity.

A base supporting member 440 to which the X-ray irradiator 400 is coupled is installed on an upper surface of the frame 100. Preferably, the X-ray imaging apparatus according to the present invention is configured to further include a chin rest 600 which is installed to the frame 100 so as to be disposed at the one end portion side of the X-ray irradiator 400.

The chin rest 600 is used to support the chin of a user, that is, a patient so as to improve patient's convenience during the X-ray imaging and to stably perform the X-ray imaging.

In addition, it is preferable that the X-ray irradiator 400 is coupled to the base supporting member 440 so as to be rotated around the rotation axis extending in the longitudinal direction, so that the X-ray irradiation hole 410 can be rotated a full 360 degrees to be positioned freely at any position. The X-ray irradiation hole 410 is opened at the one end portion of the X-ray irradiator 400 outward from the oral cavity so as to irradiate the X-ray toward the position of the imaging object tooth.

A camera unit 300 is installed in the X-ray irradiator 400 to image the interior of the oral cavity. The camera unit 300 is connected to a monitor unit 310 to transmit the captured image to the monitor unit 310. Preferably, a light source is installed in the X-ray irradiator 400 to illuminate the interior of the oral cavity.

Namely, the camera unit 300 images the interior of the oral cavity of a patient to transmits the image to the monitor unit 310, so that the teeth inside the oral cavity can be identified and the position of the imaging object tooth can be accurately recognized.

Figure 2:
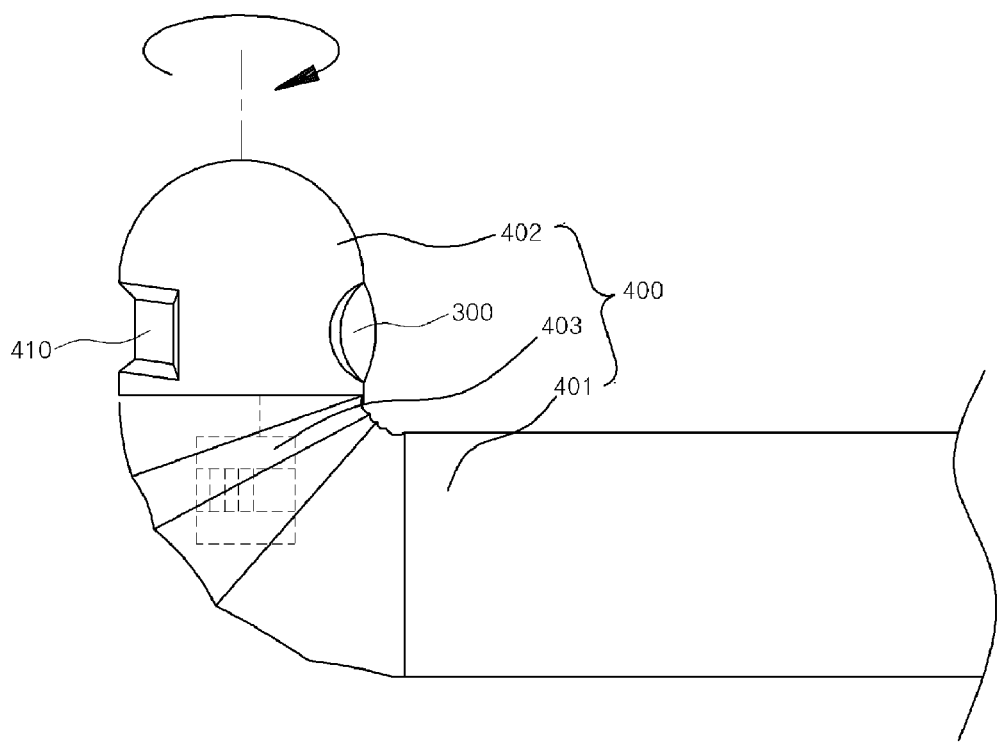
FIGS. 2 to 5 are diagrams illustrating an X-ray irradiator according to the embodiment of the present invention.

Referring to FIG. 2, the X-ray irradiator 400 is configured to include a main body 401 which is disposed to be inserted into the oral cavity in the longitudinal direction thereof, an X-ray irradiation body 402 which is protruded from the end portion of the main body 401 upward or downward and is rotatably coupled to the main body 401 and in which an X-ray irradiation hole 410 is formed, and an irradiation body rotation motor 403 which is installed inside the main body 401 to rotate the irradiation body 402. The X-ray irradiation body 402 is rotated according to operations of the irradiation body rotation motor 403.

In addition, the camera unit 300 is installed in the X-ray irradiation body 402, and the camera unit 200 and the X-ray irradiation hole 410 are arranged with an angle difference around the rotation center of the X-ray irradiation body 402. As an example, the camera unit 300 and the X-ray irradiation hole 410 are arranged on the same circumference in the X-ray irradiation body 402. In addition, as another example, the camera unit 300 and the X-ray irradiation hole 410 are arranged at the opposite positions, that is, at the positions with an angle difference of 180 degrees on the same circumference in the X-ray irradiation body 402.

Figure 3:
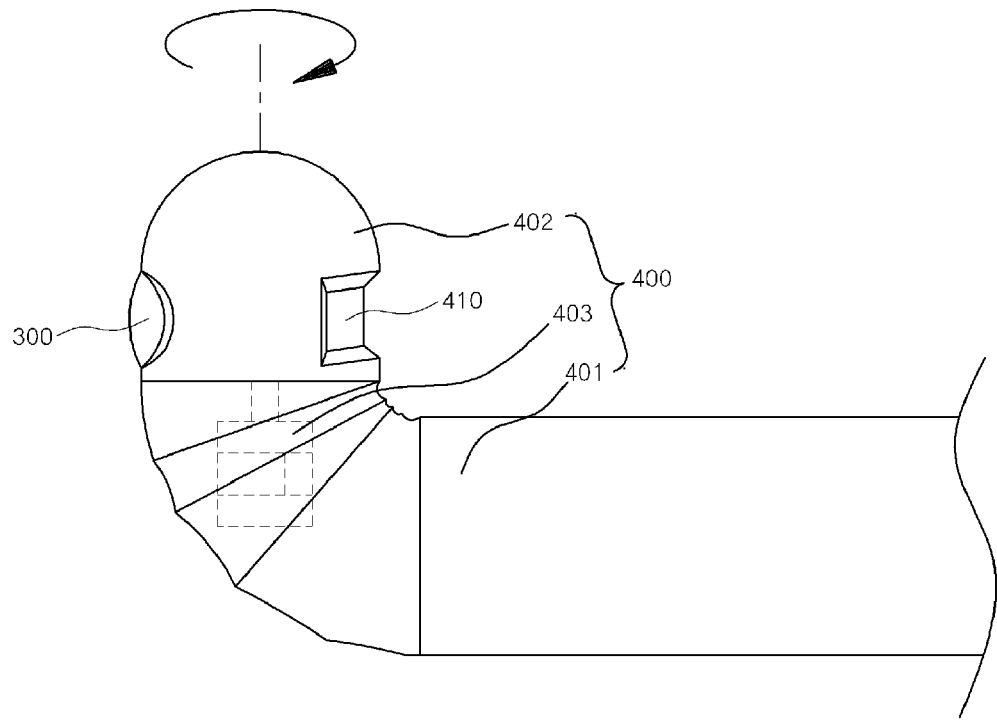

In the above example, in the state where the X-ray irradiation body 402 is inserted into the oral cavity, the camera unit 300 is located toward the tooth, and the camera unit 300 images the tooth to identify the position of the X-ray imaging object tooth. Next, referring to FIG. 3, the X-ray irradiation body 402 is rotated to the position, where the position of the tooth was identified by the camera unit 300, 180 degrees by the irradiation body rotation motor 403, so that the X-ray irradiation hole 410 is located at the position where the camera unit 300 was located to identify the position of the tooth.

Therefore, the X-ray irradiation hole 410 is accurately located at the position identified by the camera unit 300 to irradiate the X-ray toward the imaging object tooth.

On the other hand, an aperture diaphragm for adjusting the aperture size of the X-ray irradiation hole 410 is installed in the X-ray irradiation hole 410. The aperture diaphragm adjusts the aperture size of the X-ray irradiation hole 410 according to the imaging range corresponding to the sizes and number of the teeth identified by the camera unit 300 to adjust the irradiation amount of the X-ray irradiated through the X-ray irradiation hole 410.

Figure 4:
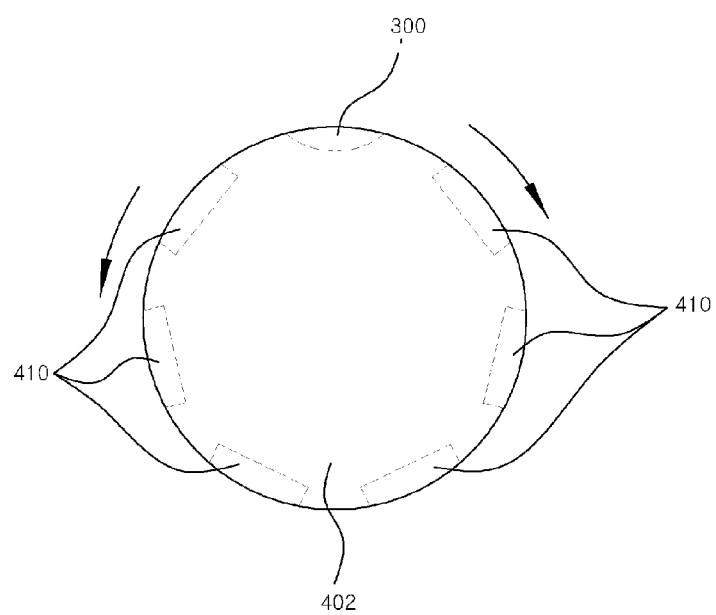

In addition, referring to FIG. 4, a plurality of the X-ray irradiation holes 410 having different sizes may be arranged to be separated from each other with angle differences from the camera unit 300 around the rotation center of the X-ray irradiation body 402 so as to irradiate different X-ray doses.

Namely, the X-ray irradiation hole 410 which irradiates the X-ray dose corresponding to the imaging range according to the sizes and number of the teeth is selected among a plurality of the X-ray irradiation holes 410 by adjusting the angle of a rotation body 800 rotated by a rotation unit 900 according to the imaging range identified by the camera unit 300, so that the X-ray can be irradiated.

IN addition, a plurality of the X-ray irradiation holes 410 can be individually opened and closed, so that only the X-ray irradiation hole 410 directing the imaging object tooth is opened and the other X-ray irradiation holes are closed.

In this manner, the X-ray imaging object tooth is identified by the camera unit 300, and the X-ray is irradiated by the X-ray irradiator 400 with the X-ray irradiation amount according to the imaging range of the imaging object tooth, so that it is possible to minimize the radiation exposure dose applied from the interior of the human body to the human body.

Figure 5:
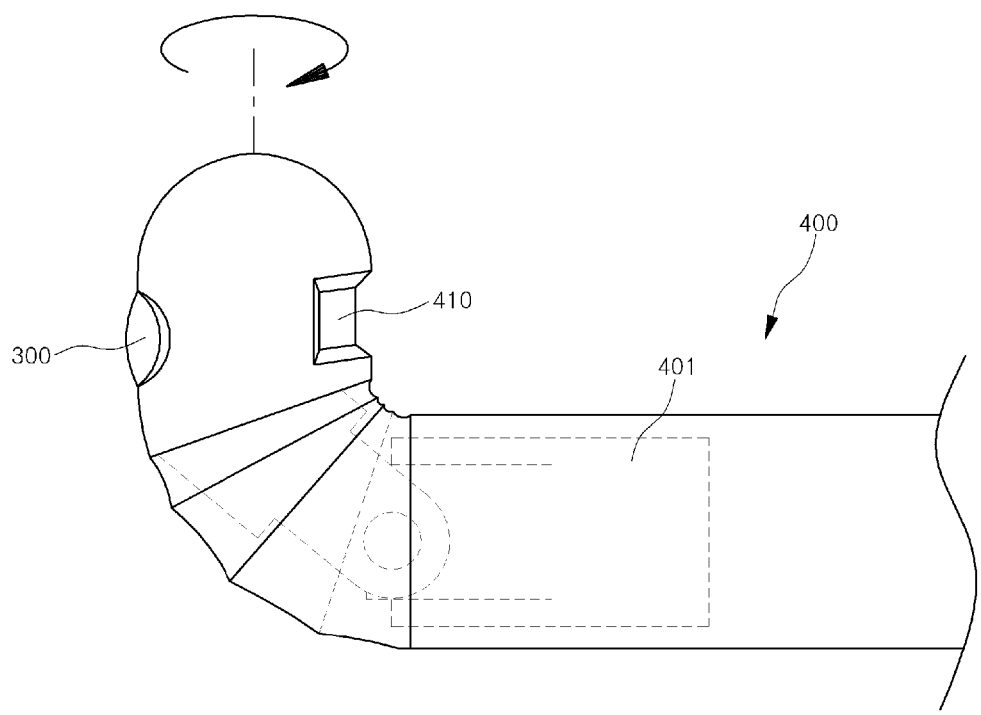

Referring FIG. 5, preferably, the X-ray irradiation body 402 is tiltably coupled to the main body 401 in various manners such as universal joint or ball-and-socket joint.

Since the angle between the main body 401 and the X-ray irradiation body 402 can be adjusted, the X-ray irradiator 400 can accurately irradiate the X-ray toward the imaging object tooth by adjusting the angle of the X-ray irradiation body 402 according to the position of the imaging object tooth inside the oral cavity.

An X-ray light source (not shown) with a collimator for X-ray irradiation is installed inside the X-ray irradiator 400. The X-ray generated by the X-ray light source is irradiated in a reference direction through the X-ray irradiation hole 410 formed in the X-ray irradiator 400. Herein, the reference direction denotes the direction from the X-ray irradiator 400 toward the imaging object tooth.

The intraoral X-ray imaging apparatus having a camera according to the present invention is configured to include an X-ray detector 500 which detects the X-ray irradiated by the X-ray irradiator 400 outside the oral cavity.

Figure 6:
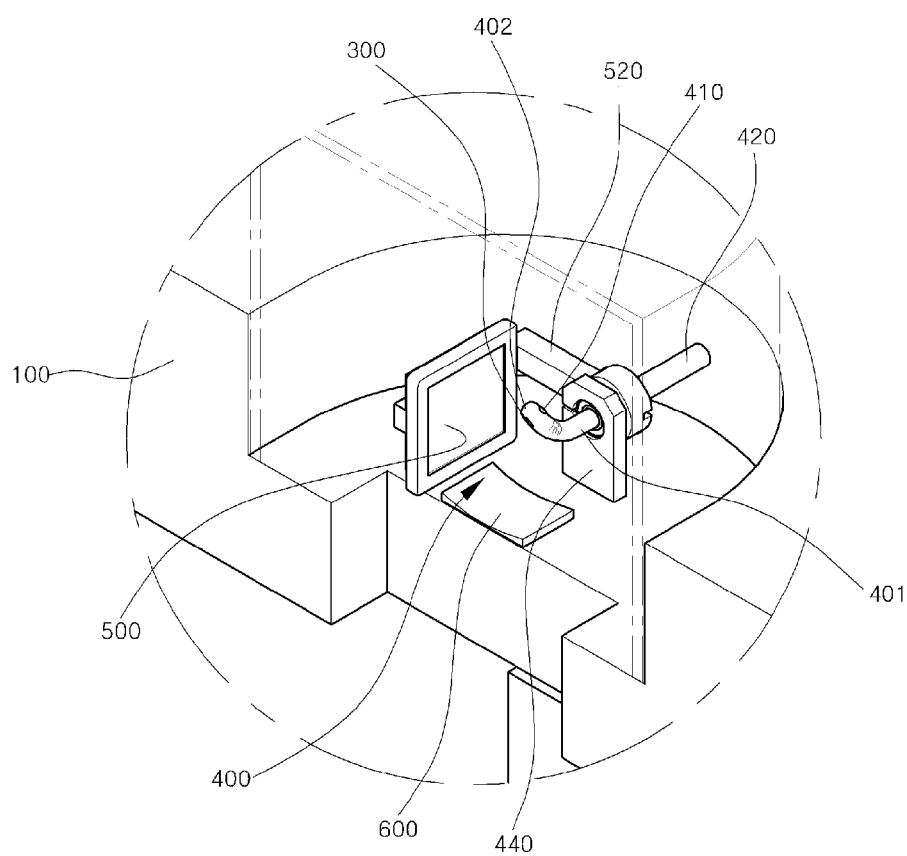
FIG. 6 is an enlarged perspective diagram illustrating main components of the present invention.

The X-ray detector 500 is arranged to be separated from the X-ray irradiator 400 in the frame 100 so that the X-ray detector 500 can be moved so as for the distance to the X-ray irradiator 400 to be adjusted. Referring to FIG. 6, the X-ray imaging apparatus according to the present invention is configured to further include a supporting arm 520 which connects the X-ray irradiator 400 and the X-ray detector 500. The X-ray detector 500 is movably connected to the supporting arm 520 so that the distance to the X-ray irradiator 400 can be adjusted.

The X-ray detector 500 is arranged to face the X-ray irradiation hole 410 of the X-ray irradiator 400. The X-ray detector 500 and the X-ray irradiator 400 are integrally connected to each other through the supporting arm 520, so that the X-ray detector 500 is rotated when the X-ray irradiator 400 is rotated in the base supporting member 440.

Namely, when the position of the X-ray irradiation hole 410 is changed according to the rotation of the X-ray irradiator 400, the X-ray detector 500 is rotated together with the X-ray irradiator 400, so that the state where the X-ray detector 500 faces the X-ray irradiator 400 is maintained.

Therefore, the X-ray emitted from the X-ray irradiator 400 is irradiated perpendicularly to the X-ray detector 500.

Figure 7:
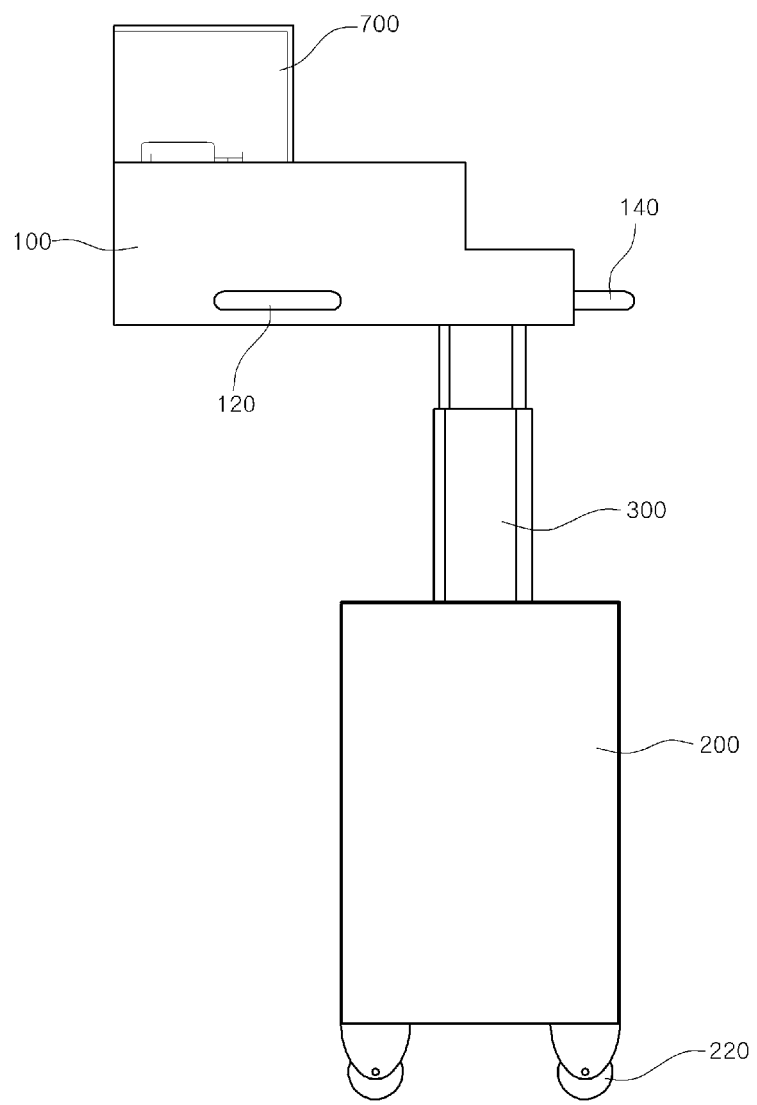
FIG. 7 is a side diagram illustrating an example where an elevating unit is installed in the present invention.

On the other hand, referring to FIG. 7, the frame 100 is coupled to the elevating unit 210, and the elevating unit 210 is coupled to the lower frame 200. Namely, the frame 100 is coupled to the one end of the elevating unit 210 in the longitudinal direction, and the lower frame 200 is coupled to the other end thereof in the longitudinal direction. The elevating unit 210 may be configured by employing a hydraulic cylinder or the like as a supporting means which can be extended in the longitudinal direction.

In addition, castors 220 are attached to the bottom of the lower frame 200 so as to allow the frame 100 to be freely moved.

Therefore, the height of the frame 100 can be adjusted according to the height of a patient in order to capture the image of a tooth of the patient. In addition, the frame 100 can be moved to a desired site by using the castors 220 and a movement grip 140, so that a degree of space utilization can be maximized.

The X-ray detector 500 is moved so that the distance to the X-ray irradiator 400 is adjustable. The X-ray detector 500 is arranged to be in close contact with the face of a patient, so that the distance to the X-ray imaging object, that is, the tooth is minimized.

It is preferable that the distance between the X-ray imaging object, that is, the tooth and the X-ray detector 500 is as small as possible during the X-ray imaging. This is because the X-ray imaging with substantially actual magnification of the tooth, that is, magnification 1:1 of the tooth can be performed when the X-ray detector 500 approaches closest to the object. In addition, when several teeth are to be imaged, the magnifications of the teeth need to be constant in order to accurately compare and identify the teeth. Therefore, it is preferable that the imaging is performed with constant magnifications. In order to maintain constant magnifications, the distance (ODD: object detector distance) between the X-ray imaging object, that is, the tooth and the X-ray detector 500 needs to be constant.

Therefore, during the X-ray imaging, the X-ray detector 500 is moved so as to be in close contact with the face of a patient, so that the distance between the tooth and the X-ray detector 500 is minimized and the distance between each of the different teeth and the tooth and the distance between each of the different teeth and X-ray detector 500 are maintained substantially constant.

Figure 8:
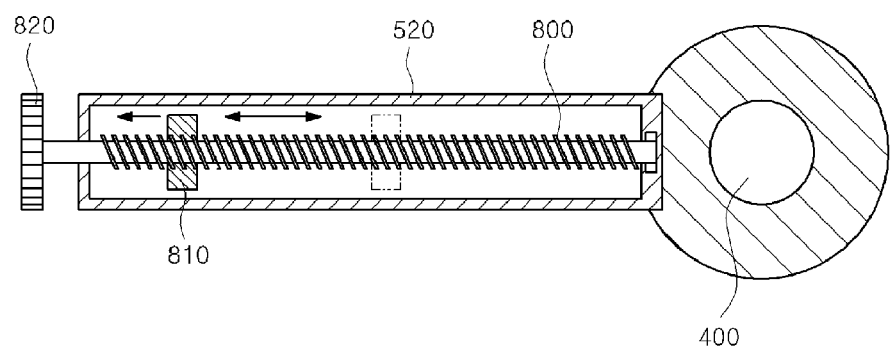
FIG. 8 is a cross-sectional diagram illustrating an example where an X-ray detector of the present invention is configured so that the X-ray detector can be moved.

Referring to FIG. 8, the X-ray detector 500 is coupled to the supporting arm 520 so as to be moved in the longitudinal direction of the supporting arm 520. The X-ray imaging apparatus according to the present invention is configured to include a screw 800 which is installed in the longitudinal direction of the supporting arm 520 so as to be rotatably supported and a detector supporting member 810 which is screw-engaged with the screw 800 so as to be moved in the longitudinal direction of the supporting arm 520 and to which the X-ray detector 500 is connected.

Preferably, a handle 820 for manipulation of rotating the screw 800 is installed to the end portion of the screw 800. In addition, preferably, the X-ray imaging apparatus according to the present invention is configured to include a screw rotating motor 830 which is connected to the screw 800 to rotate the screw 800 in normal and counter directions, a sensor 840 which is installed to the X-ray detector 500 to sense the contact of the X-ray detector 500 with the face, and a motor controller 850 which is connected to the screw rotating motor 830 and the sensor 840 to control operations of the screw rotating motor 830.

The detector supporting member 810 is screw-coupled to the screw 800 so as to be moved according to the rotation direction of the screw 800. Namely, the X-ray detector 500 together with the detector supporting member 810 is moved according to the rotation of the screw 800 so as to be in close contact with the face. When the detector supporting member 810 is moved to be in close contact with the face, the sensor 840 senses the close contact with the face and notifies the motor controller 850 of the contact state, and thus, the motor controller 850 allows the screw rotating motor 830 to stop.

In addition, in the present invention, the supporting arm 520 is configured so that the length thereof can be adjusted. Therefore, the distance between the X-ray irradiator 400 and the X-ray detector 500 can be adjusted.

Although not shown, the supporting arm 520 may be configured by employing a length-adjustable unit such as a hydraulic cylinder. In addition, the supporting arm 520 may be configured with a length-adjustable structure where multi-stages of hollow tubes are inserted in an extractable manner.

The X-ray detector 500 is moved by adjusting the length of the supporting arm, so that the X-ray detector 500 is in close contact with the face of a patient.

Figure 9:
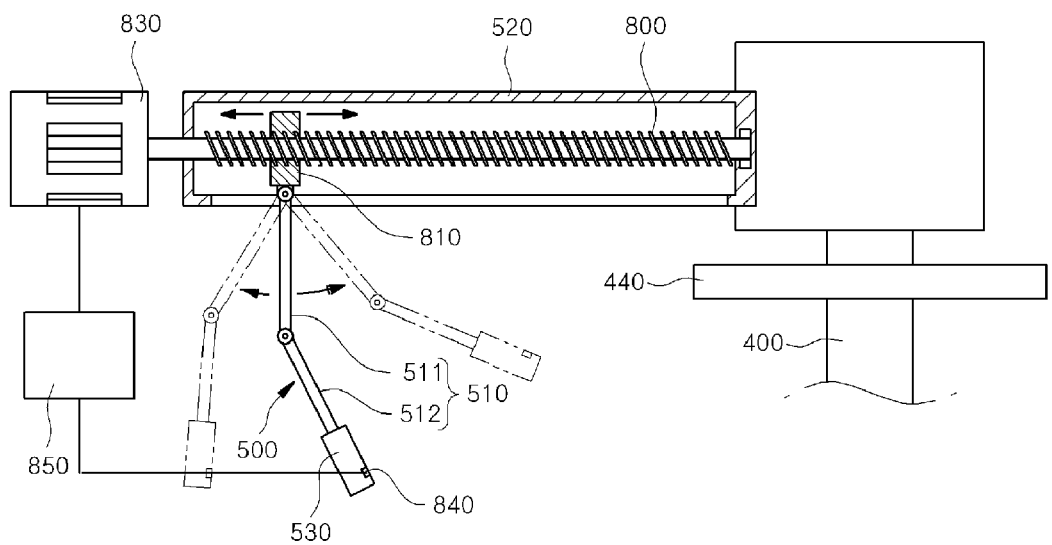
FIGS. 9 and 10 are plan diagrams illustrating an example where an X-ray detector of the present invention is configured so that an angle thereof can be adjusted.
Figure 10:
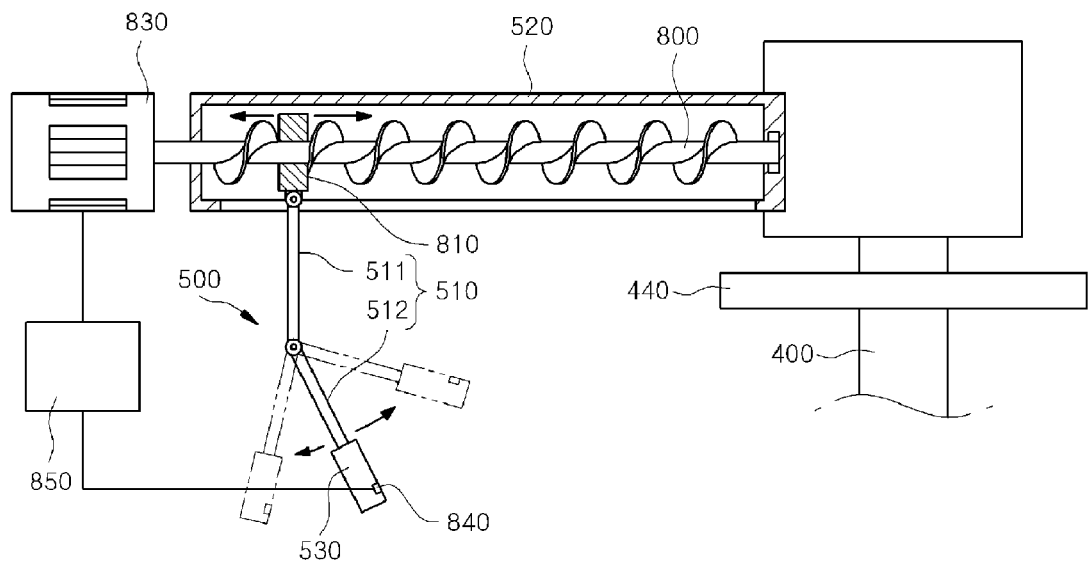

In addition, referring to FIGS. 9 and 10, the X-ray detector 500 is configured to include a link member 510 of which the one side is rotatably connected to the supporting arm 520 and a detection panel member 530 which is installed to the other side of the link member 510 to detect the X-ray.

The link member 510 is rotatably connected to the supporting arm 520 so that the angle of the link member 510 is adjusted.

After the X-ray detector 500 is moved to be in closest contact with the face of a patient, the detection panel member 530 is located at the more accurate X-ray imaging position by adjusting the angle of the link member 510.

The link member 510 is configured to include a first link 511 which is connected to the supporting arm 520 and a second link 512 of which the one side is rotatably connected to the first link 511 through a hinge connector 513 and the other side is connected the detection panel member 530.

The link member 510 is configured so that the angle of the second link 512 can be separately adjusted by the hinge connector 513 of the first link 511 and the second link 512. The X-ray detector 500 is configured so that the detection panel member 530 can be located at the more accurate X-ray imaging position by adjusting the angle of the first link 511 and the angle of the second link 512 and so that the X-ray detector 500 is in close contact with the face with as large an area as possible to stably perform the X-ray imaging.

It is preferable that the hinge connector 513 between the first link 511 and the second link 512 is elastically supported. The hinge connector 513 is configured to include a return spring (not shown) of which the one end is fixed to the rotation axis of the first link 511 and of which the other end is fixed to the rotation axis of the second link 512 to elastically support the second link 512. The second link 512 is elastically supported by the hinge connector 513 in the state where the second link 512 is inclined in the direction toward the face of a patient, so that the detection panel member 530 can be securely in contact with the face of a patient by adjusting the angle thereof in the elastically supported state.

In addition, the X-ray detector 500 may be used in a manner where the X-ray detector 500 is detached from the frame 100.

Figure 11:
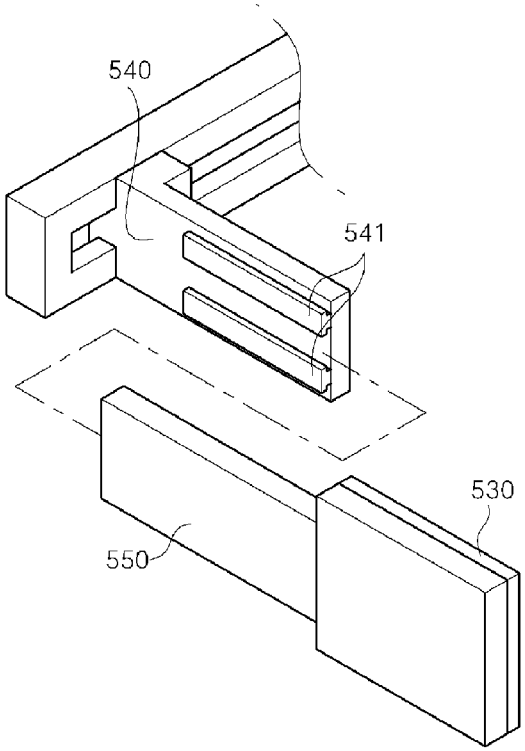
FIG. 11 is a partial enlarged perspective diagram illustrating an example where an X-ray detector of the present invention is configured so that the X-ray detector can be separated.

As an example, the X-ray detector 500 is detachably connected to the supporting arm 520. Namely, referring to FIG. 11, the X-ray detector 500 is configured to include a fixing arm 540 which is connected to the supporting arm 520 and a mounting arm 550 which is detachably connected to the fixing arm 540 and in which a detection panel member 530 capable of detecting X-ray is installed.

For example, arm insertion rails 541 are formed in the fixing arm 540 so that a mounting arm 550 is inserted into the arm insertion rails 541 in the longitudinal direction thereof. For example, the mounting arm 550 is detachably coupled so that the mounting arm 550 is detached from the end side of the fixing arm 540 through the arm insertion rails 541 in the longitudinal direction of the fixing arm 540.

In the case where the X-ray image is performed on the portion where it is difficult to allow the detection panel member 530 to be in close contact with the face of a patient, the X-ray detector 500 is configured so that the mounting arm 550 is detached from the fixing arm 540 and the detection panel member 530 is easily allowed to in close contact with the face of a patient.

Figure 12:
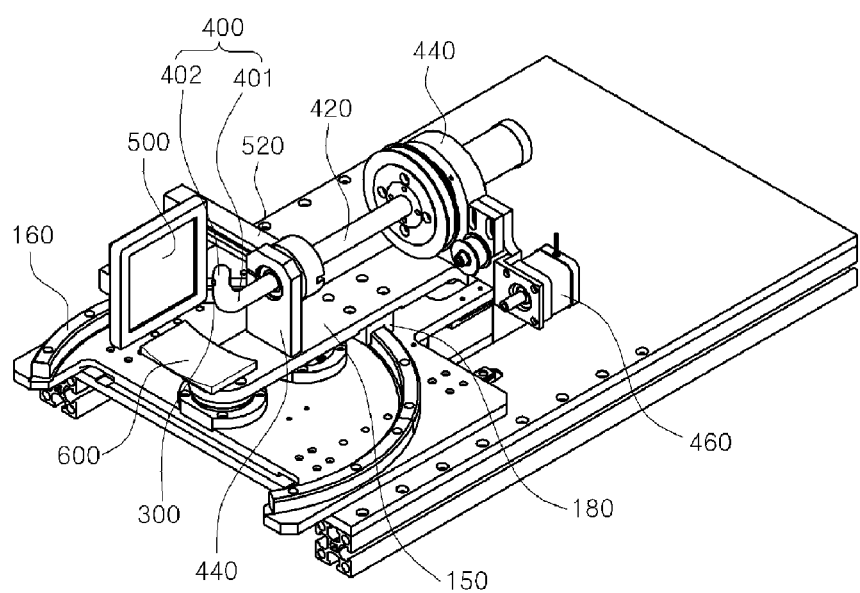
FIGS. 12 and 13 are partial enlarged perspective diagrams illustrating the interior of the frame illustrated in FIG. 1.
Figure 13:
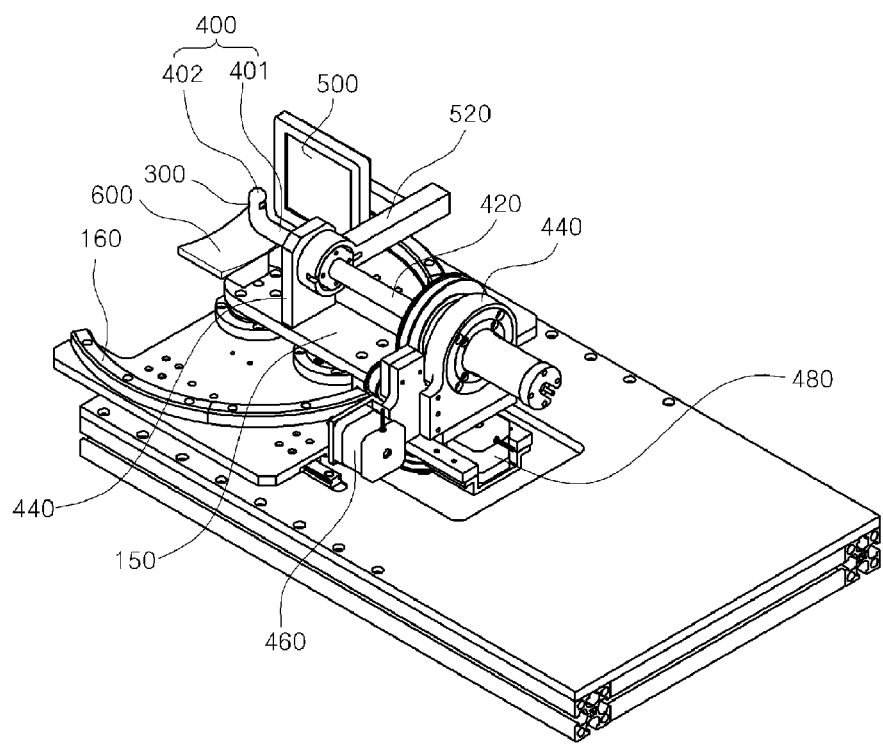

On the other hand, according to the present invention, the X-ray irradiator 400 can be rotated around the longitudinal direction as a rotation axis in the left and right directions. Referring to FIGS. 12 and 13, the X-ray irradiator 400 is rotatably coupled to the base supporting member 440 to pass through the base supporting member 440, and an extension bar 420 is protruded from the rear side thereof. The X-ray irradiator 400 and the X-ray detector 500 are always integrally moved due to the supporting of the supporting arm 520, so that the X-ray emitted from the X-ray irradiator 400 is always irradiated on the X-ray detector 500. The X-ray irradiator 400 is rotated by a first driving unit 460 which transmits power to the extension bar 420 by using power transmitting means such as gear and pulley.

Figure 14:
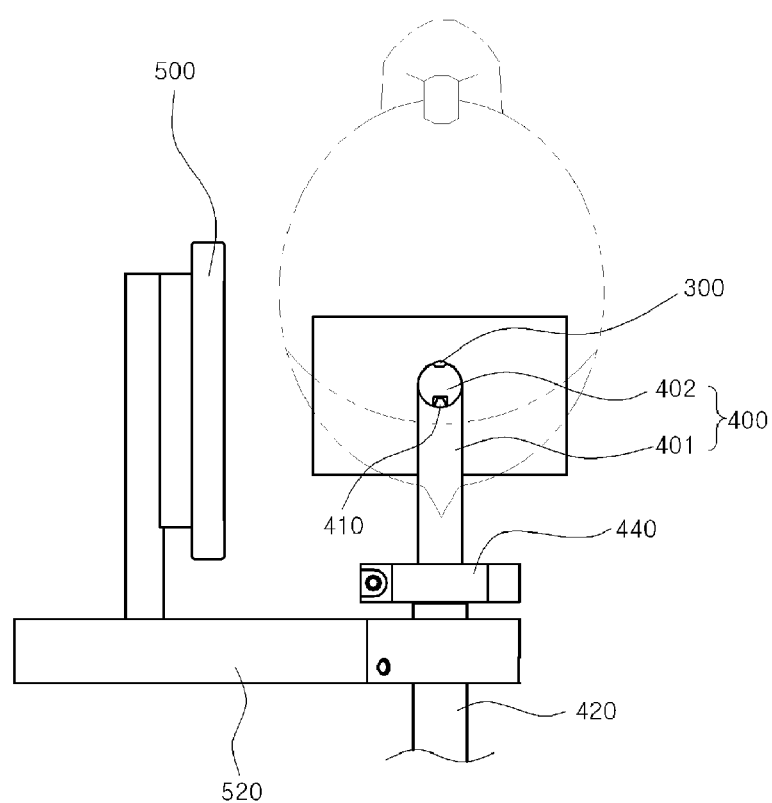
FIGS. 14 to 16 are schematic diagrams illustrating a state according to a change in irradiation angle of the X-ray detector with respect to the head of a patient.
Figure 15:
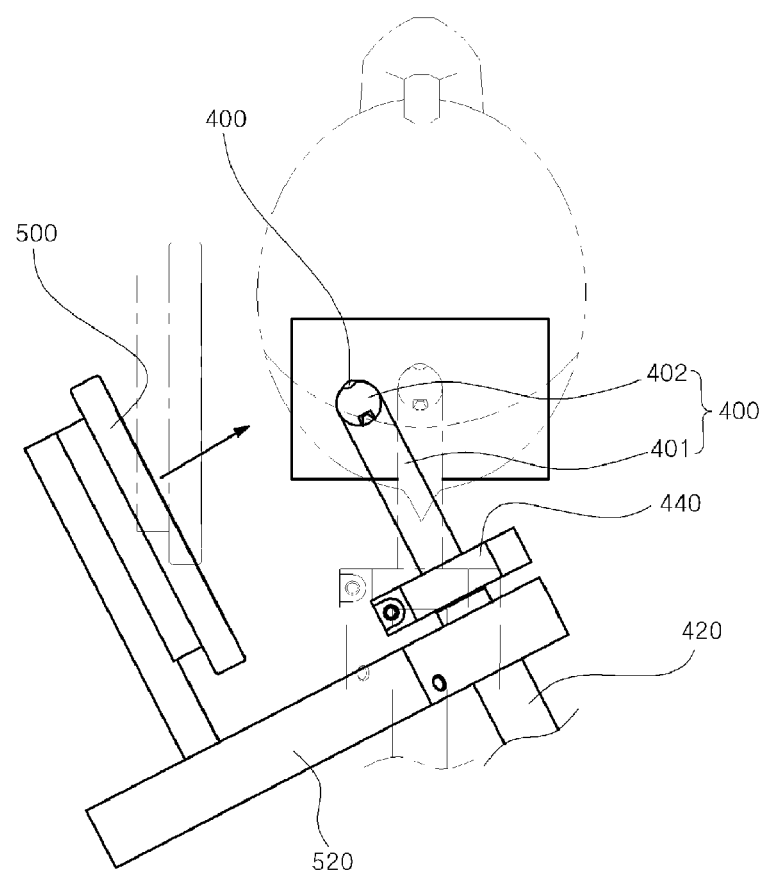
Figure 16:
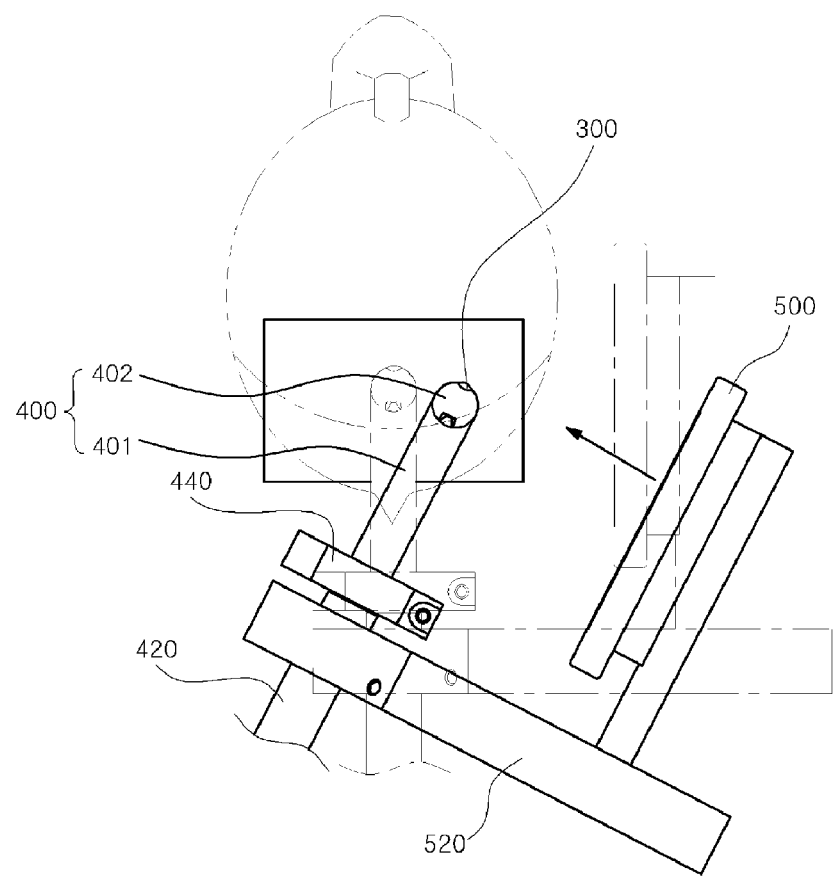

Namely, as illustrated in FIGS. 14 to 16, since the X-ray irradiator 400 can irradiates X-ray on the imaging object tooth at various irradiation angles, images of the tooth imaged at the various angles can be obtained so as to be used for dental treatment of a patient.

In addition, the X-ray imaging apparatus is configured to further include a base plate 150 which is movably installed in an upper portion of the frame 100 and on which the base supporting member 440 is installed.

In addition, the base plate 150 is configured to include a guide block 180 having a groove formed in the lower portion thereof, so that the base plate 150 is moved in the state where the guide rail 160 coupled to the frame 100 is inserted into the groove of the guide block 180. Herein, the guide rail 160 may have various shapes. Preferably, the guide rail 160 is formed to have an arc shape.

In addition, the X-ray irradiator 400 can be moved by a second driving unit 480 which transmits power to the base plate 130 by using driving means such as gear and pulley.

The teeth of a person are arranged in a semicircular shape. The irradiation directions of the X-ray irradiator 400 for imaging the teeth need to be coincident with the directions toward the imaging object teeth. Namely, even in the state where the X-ray irradiator 400 is located inside the oral cavity, the X-ray irradiator 400 is moved along the arc-shaped guide rail 160 so as to allow the X-ray irradiation direction to coincident with the direction toward the imaging object tooth, so that the imaging object tooth can be accurately imaged.

An imaging method using the intraoral X-ray imaging apparatus having a camera according to the present invention is configured to include an irradiator insertion step S1 of inserting an end portion of the X-ray irradiator 400 which is supported by the frame and irradiates X-ray through the X-ray irradiation hole 410 formed on the end portion thereof into the oral cavity of a patient, an imaging object tooth identification step S2 of checking an image captured by the camera unit 300 installed in the X-ray irradiator 400 through a monitor unit 210 to identify the imaging object tooth, an irradiation hole movement step S3 of locating the X-ray irradiation hole 410 at the position identified by the camera unit 300, a detector arrangement step S4 of arranging the X-ray detector 500 outside the oral cavity so as to detect the X-ray irradiated from the X-ray irradiator 400, and an imaging step S5 of allowing the X-ray detector 500 to detect the X-ray irradiated through the X-ray irradiation hole 410 from the X-ray irradiator 400.

In the irradiator insertion step of the imaging method using the intraoral X-ray imaging apparatus having a camera according to the present invention, the position of the X-ray imaging object tooth is identified by the camera unit 300, and after that, the X-ray irradiator 400 is allowed to irradiate the X-ray on the imaging object identified by the camera unit 300.

Figure 17:
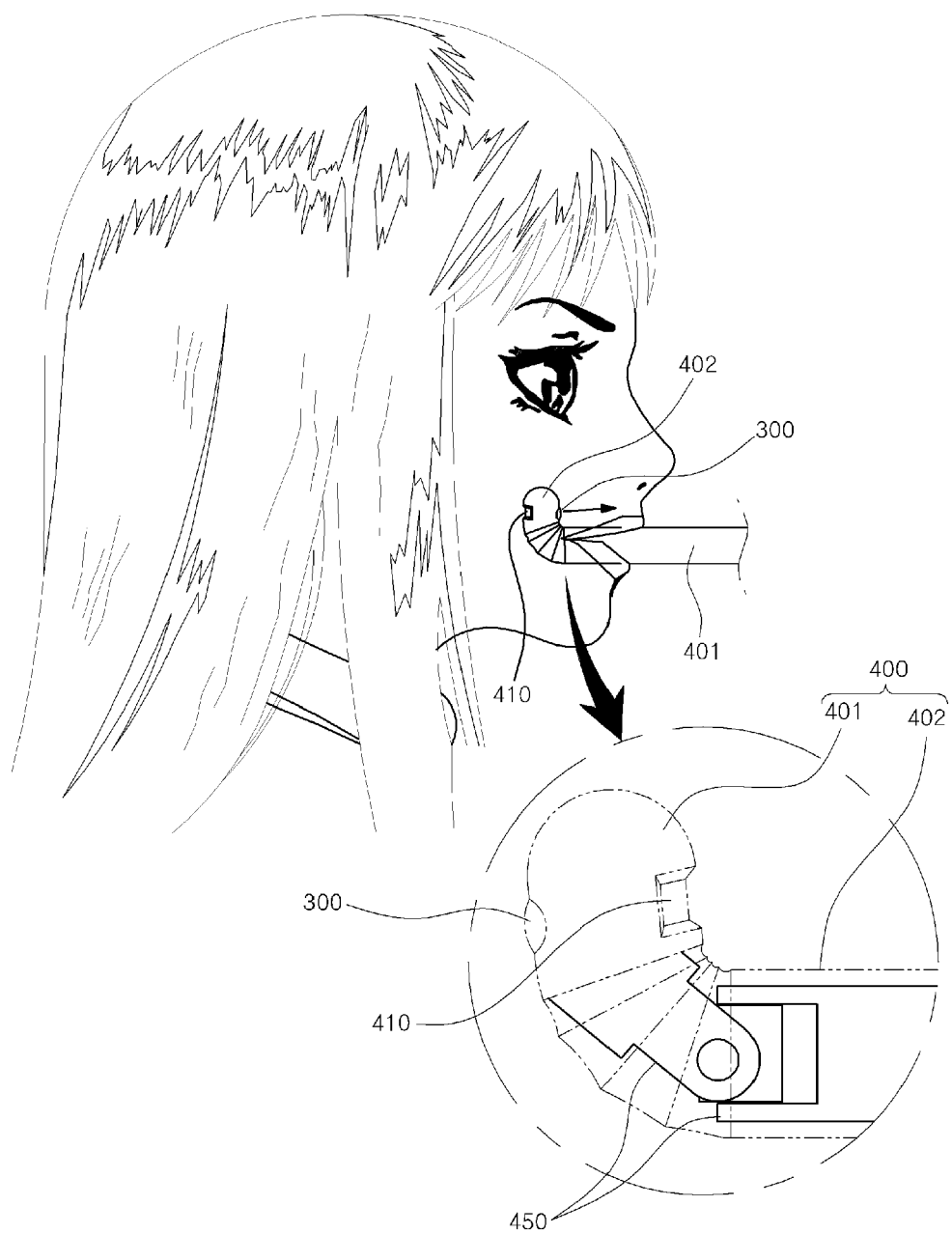
FIGS. 17 and 18 are schematic diagram and partial enlarged diagram illustrating an example where imaging is performed while adjusting an irradiation angle of the X-ray irradiator.
Figure 18:
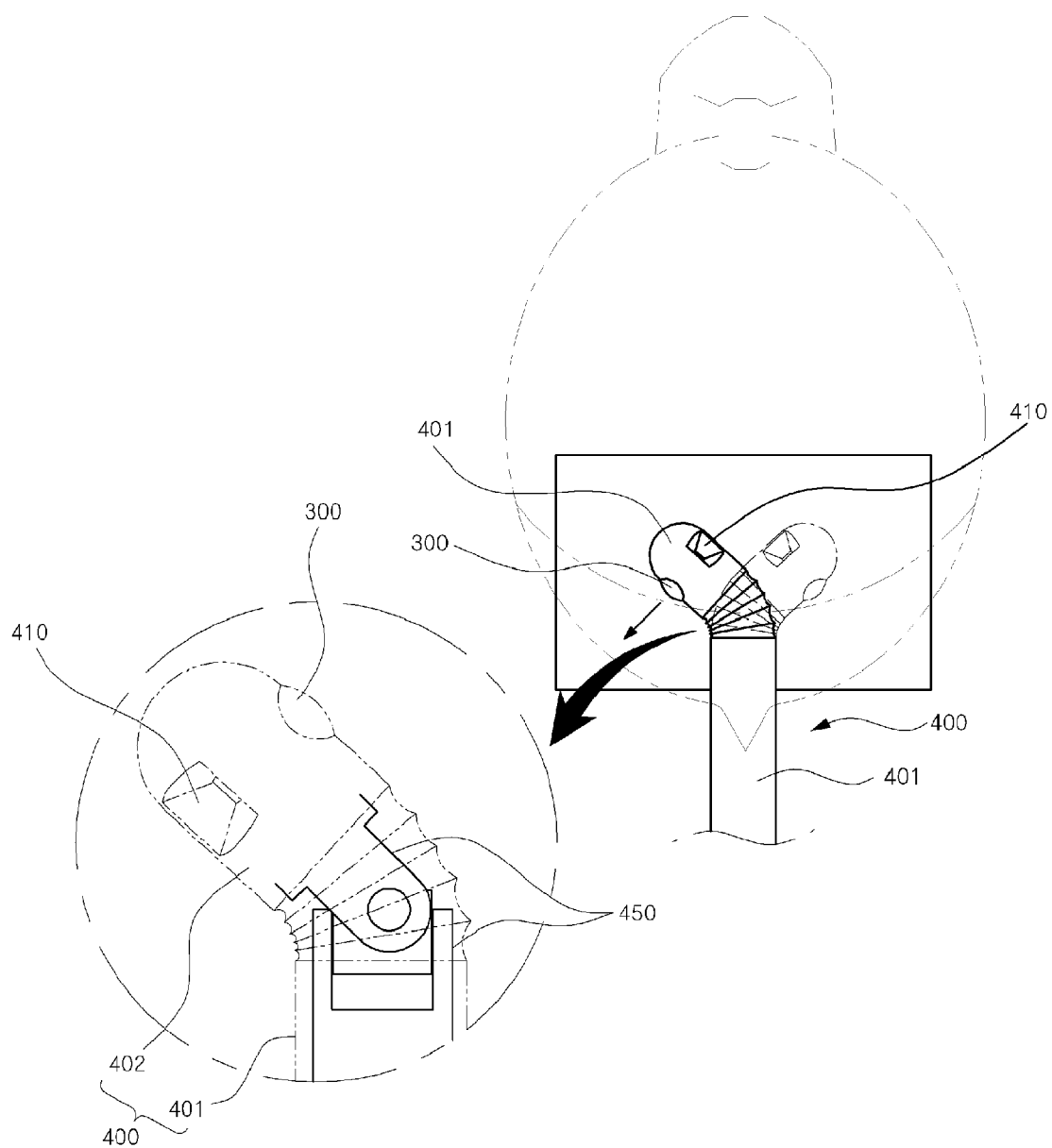

Namely, referring to FIGS. 17 and 18, in the state where the camera unit 300 is located in the X-ray irradiation body 402 toward the tooth, the X-ray imaging object tooth is identified by the camera unit 300, and after that, the X-ray irradiation body 402 is rotated 180 degrees, so that the X-ray irradiator 400 is located at the position corresponding to the position where the camera unit 300 is to capture the image. Next, the X-ray is irradiated by the X-ray irradiator 400, so that the image of the X-ray imaging object tooth can be captured by the camera unit 300.

In addition, the direction of the camera unit 300 and the direction of the X-ray irradiation hole 410 can be changed into various directions by adjusting the angle of the X-ray irradiation body 402, so that it is possible to easily check the state of the teeth inside the oral cavity and to accurately image the teeth.

In this manner, the reference direction of the X-ray irradiation inside the oral cavity is adjusted, so that the X-ray imaging object tooth can be accurately imaged.

In addition, the X-ray irradiator 400 and the X-ray detector 500 are arranged to face each other and are integrally connected to each other through the supporting arm 520. In the detector arrangement step S2, when the X-ray detector 500 is to be arranged, the X-ray detector 500 and the X-ray irradiator 400 are integrally moved, so that the X-ray detector 500 and the X-ray irradiator 400 are arranged to face each other.

Therefore, there is no need to adjust the position of the X-ray irradiator 400 again according to the position of the X-ray detector 500.

In addition, the detector adjustment step includes a step of adjusting the angle of the moved X-ray detector 500 so as to allow the X-ray detector 500 to be in close contact with the face of a patient.

In this manner, by using the imaging method using the intraoral X-ray imaging apparatus having a camera according to the present invention, it is possible to select only the tooth of interest and to obtain images thereof at various angles.

In addition, in the imaging method using the intraoral X-ray imaging apparatus having a camera according to the present invention, it is possible to accurately only the X-ray imaging object tooth among the teeth of a patient, and since imaging is not performed again, it is possible to minimize a radiation exposure dose applied to the head of a patient.

In addition, the distance between the X-ray irradiator 400 and the X-ray detector 500 is minimized, so that it is possible to obtain images of portions of the tooth with constant magnifications and to obtain accurate images without distortion.

While the present invention has been particularly shown and described with reference to exemplary embodiments of an intraoral X-ray imaging apparatus having a camera, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. An intraoral X-ray imaging apparatus having a camera, comprising:
   a frame;
   an X-ray irradiator which is installed to be supported by the frame, wherein the X-ray irradiator includes a main body disposed to be inserted into an oral cavity in a longitudinal direction of the main body; an X-ray irradiation body protruding from one end portion of the main body and rotatably coupled to the main body; and an irradiation body rotation motor installed inside the main body to rotate the X-ray irradiation body;
   an X-ray irradiation hole formed in the X-ray irradiation body, an X-ray being irradiated through the X-ray irradiation hole;
   a camera unit installed in the X-ray irradiation body to image an interior of the oral cavity, wherein the camera unit and the X-ray irradiation hole are arranged at different angular positions around a rotation center of the X-ray irradiation body;
   a monitor unit which is connected to the camera unit to output the image captured by the camera unit; and
   an X-ray detector which is arranged outside the oral cavity to be separated from the X-ray irradiator in the frame so as to detect the X-ray irradiated from the X-ray irradiator.

2. The intraoral X-ray imaging apparatus according to claim 1, wherein a light source is installed in the X-ray irradiator to illuminate the interior of the oral cavity.

3. The intraoral X-ray imaging apparatus according to claim 1, wherein the X-ray irradiation body is tiltably connected to the one end of the main body.

4. The intraoral X-ray imaging apparatus according to claim 1, wherein an aperture diaphragm for adjusting an aperture size of the X-ray irradiation hole is installed in the X-ray irradiation hole.

5. The intraoral X-ray imaging apparatus according to claim 1, wherein the X-ray irradiation hole includes a plurality of X-ray irradiation holes having different sizes, and the plurality of the X-ray irradiation holes are arranged at different angular positions around the rotation center of the X-ray irradiation body so as to irradiate different X-ray doses.

6. The intraoral X-ray imaging apparatus according to claim 5, wherein the plurality of the X-ray irradiation holes can be individually opened and closed.

7. The intraoral X-ray imaging apparatus according to claim 1, wherein the camera unit and the X-ray irradiation hole are arranged at the different angular positions of 180-degree on a same circumference in the X-ray irradiation body.

8. The intraoral X-ray imaging apparatus according to claim 1, further comprising a supporting arm which connects the X-ray irradiator and the X-ray detector,
   wherein the X-ray detector is coupled to the supporting arm so as to be moved in a longitudinal direction of the supporting arm.

9. The intraoral X-ray imaging apparatus according to claim 8, wherein the X-ray detector includes a link member, one side of which is rotatably connected to the supporting arm, and on the other side of which a detection panel member is installed to detect the X-ray.

10. The intraoral X-ray imaging apparatus according to claim 9, wherein the link member includes a first link which is connected to the supporting arm and a second link, one side of which is rotatably connected to the first link through a hinge connector and the other side of which is connected to the detection panel member.

11. The intraoral X-ray imaging apparatus according to claim 10, wherein the hinge connector elastically supports the second link.

12. The intraoral X-ray imaging apparatus according to claim 8, further comprising a base plate which is movably installed in an upper portion of the frame and on which a base supporting member coupled to the X-ray irradiator is installed,
   wherein the base plate includes a guide block having a groove formed in a lower portion thereof, so that the base plate is moved in a state where a guide rail coupled to the frame is inserted into the groove of the guide block.

13. The intraoral X-ray imaging apparatus according to claim 12, wherein the X-ray irradiator is moved by a driving unit which transmits power to the base plate by using driving means.

14. The intraoral X-ray imaging apparatus according to claim 1, further comprising a supporting arm which connects the X-ray irradiator and the X-ray detector,
   wherein a length of the supporting arm can be adjusted.

15. The intraoral X-ray imaging apparatus according to claim 14, wherein the X-ray detector includes a link member, one side of which is rotatably connected to the supporting arm, and on the other side of which a detection panel member is installed to detect the X-ray.

16. The intraoral X-ray imaging apparatus according to claim 15, wherein the link member includes a first link which is connected to the supporting arm and a second link, one side of which is rotatably connected to the first link through a hinge connector and the other side of which is connected to the detection panel member.

17. The intraoral X-ray imaging apparatus according to claim 16, wherein the hinge connector elastically supports the second link.

18. The intraoral X-ray imaging apparatus according to claim 1, further comprising:
   an elevating unit which is coupled to a lower portion of the frame; and
   a lower frame which is coupled to a lower portion of the elevating unit.

* * * * *